United States Patent [19]

Transue

[11] Patent Number: 5,249,682
[45] Date of Patent: Oct. 5, 1993

[54] PACKAGE FOR MESH ONLAY AND ATTACHED MESH PLUG

[75] Inventor: Deborah M. Transue, Bridgewater, N.J.

[73] Assignee: Ethicon, Inc., Somerville, N.J.

[21] Appl. No.: 898,055

[22] Filed: Jun. 12, 1992

Related U.S. Application Data

[63] Continuation-in-part of Ser. No. 833,275, Feb. 10, 1992.

[51] Int. Cl.⁵ .............................................. B65D 75/00
[52] U.S. Cl. .................................. 206/438; 206/483; 229/87.01
[58] Field of Search ............... 206/63.3, 438, 477–483, 206/486–489; 229/87.01, 92.8

[56] References Cited

U.S. PATENT DOCUMENTS

| | | | |
|---|---|---|---|
| 1,613,827 | 1/1927 | Hoffman | 229/87.01 |
| 2,761,557 | 9/1956 | McLean, Jr. | 206/456 |
| 3,881,674 | 5/1975 | Greene, III | 206/486 |
| 4,203,521 | 5/1980 | Dunn | 229/87.01 |
| 4,249,656 | 2/1981 | Cerwin et al. | 206/63.3 |
| 4,491,218 | 1/1985 | Aday | 206/63.3 |
| 4,496,045 | 1/1985 | Ferguson et al. | 206/63.3 |
| 4,681,226 | 7/1987 | Pretre | 206/449 |
| 4,700,833 | 10/1987 | Smith | 206/492 |
| 4,993,547 | 2/1991 | Pallasch et al. | 206/482 |
| 5,048,678 | 9/1991 | Chambers | 206/63.3 |
| 5,050,735 | 9/1991 | Levy | 206/489 |
| 5,086,914 | 2/1992 | Mish et al. | 206/63.3 |
| 5,154,284 | 10/1992 | Starkey | 206/444 |

FOREIGN PATENT DOCUMENTS 2141998 1/1985 United Kingdom ............... 206/444

Primary Examiner—Jimmy G. Foster
Attorney, Agent, or Firm—Emil Richard Skula

[57] ABSTRACT

A package for holding a medical device is disclosed. The medical device comprises a mesh onlay having a mesh plug attached perpendicularly thereto. The mesh is substantially flat and lies in a plane which is substantially horizontal with respect to the plug. The package comprises a folder which has a central floor panel for receiving the mesh onlay and mesh plug assembly. A first end panel is foldably connected to one minor side of the central panel for retaining the mesh onlay on the central panel. At least one reinforcing panel is foldably connected to the first end panel for providing structural strength to the package. A connecting panel foldably connected to the opposite minor side of the central panel is, in turn, foldably connected to an optional plug retaining panel. The optional plug retaining panel is in turn foldably connected to a second end panel. The reinforcing panel is folded outwardly and locked to the first end panel with locking means. The first end panel is locked to the central floor panel with locking means. The second end panel is locked to the central panel with locking means. The locking means for the first end panel, second end panel and each reinforcing panel comprise slots and tabs.

11 Claims, 3 Drawing Sheets

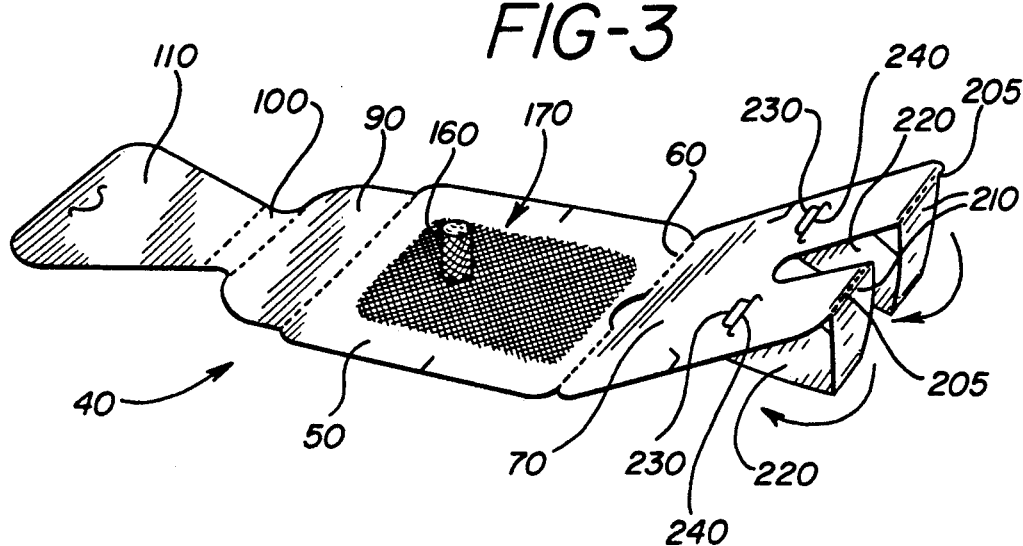
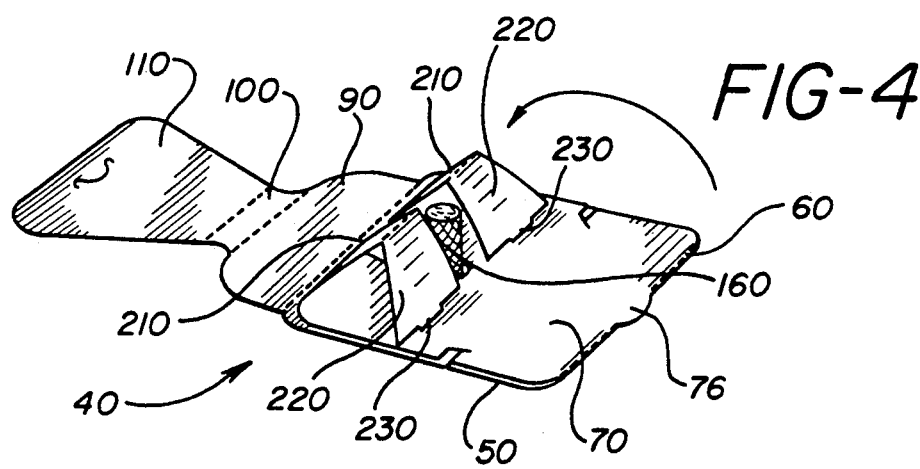
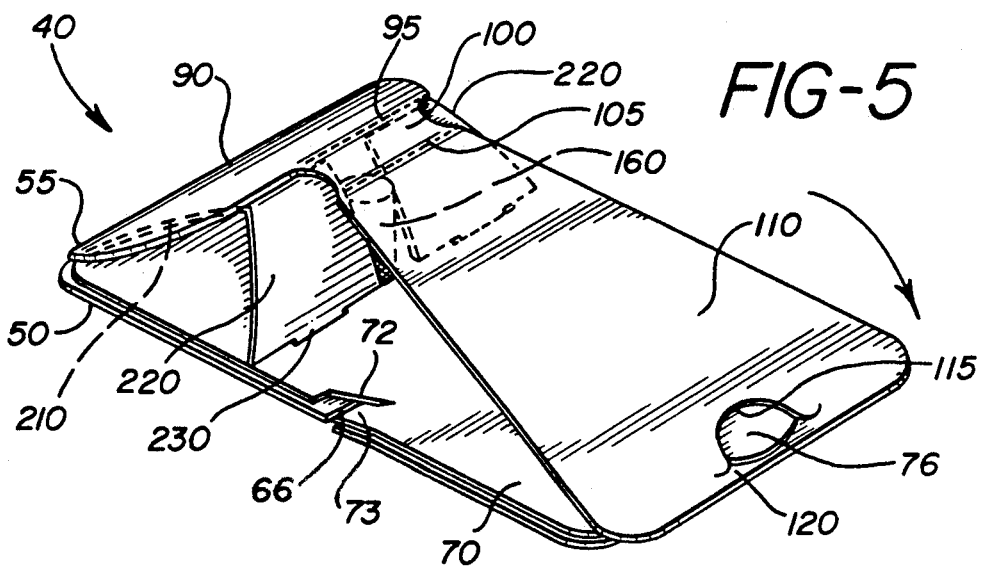

PACKAGE FOR MESH ONLAY AND ATTACHED MESH PLUG

This is a continuation-in-part application of copending, commonly-assigned patent application Ser. No. 07/833,275 filed on Feb. 10, 1992.

TECHNICAL FIELD

The technical field to which this invention relates is packaging, in particular packaging of endoscopic medical devices.

BACKGROUND OF THE INVENTION

The field of endoscopic surgery is becoming widely embraced by the medical profession. As used herein, the term "endoscopic" is defined to include endoscopic, laparoscopic, thoracoscopic and arthroscopic and similar minimally invasive surgical techniques. Endoscopic surgical techniques have resulted in benefits to both the patient and to society. By the use of endoscopic surgical techniques, the trauma of surgical procedures, ranging from rehabilitative arthroscopic knee surgery to the removal of a gall bladder or an appendix, is substantially reduced. Endoscopic surgical techniques typically require a minimal incision into the patient, thereby reducing the trauma to the patient that is associated with the radical incisions typical in conventional, open surgical techniques. In addition to the reduced trauma to the patient, the avenues for infection in an endoscopic procedure are also greatly reduced. Typically, a patient having undergone an endoscopic surgical technique will have a shorter hospital stay than a patient who has undergone a radical, conventional open surgical procedure. And, the post-operative healing time is greatly reduced. Often, the time that the patient has to spend recuperating in the hospital is reduced from more than a week to several days or less, and out-patient endoscopic surgery is becoming common. This reduction in the duration of the hospital stay and the decrease in the onset and severity of complications results in decreased costs to health insurers, employers, and patients. In addition, the risk to the patient attendant in all surgical procedures is typically reduced when endoscopic procedures are employed.

A recently developed endoscopic surgical procedure involves repairing hernias utilizing an endoscopic stapling apparatus. A particularly important hernia repair procedure relates to the repair of inguinal hernias It has been found that healing is promoted and re-occurrence of herniation is minimized by using a mesh onlay and mesh plug assembly to repair the hernia. The mesh is typically made from a biocompatible material such as polypropylene. The flat mesh typically has a plug attached perpendicular to the plane of the mesh. This plug typically consists of a roll of the mesh which is then affixed to the mesh onlay, e.g., by sutures. For insertion during a surgical procedure, the mesh onlay is typically folded about the plug and loaded into an introducer instrument, then inserted into a trocar cannula which has previously been inserted into the abdominal cavity. Next the plug and mesh onlay are located by the surgeon in the desired location proximal to the hernia. The plug is then inserted into whatever hole may be present through the inguinal canal, and the mesh onlay is stapled to the surrounding tissue.

The mesh typically used for these types of procedures tends to have a memory, therefore, it is critical that the mesh onlay be packaged in a manner such that it is retained in a substantially flat configuration, while the plug is retained in a position substantially perpendicular to the mesh.

What is needed in this art is a package for a mesh onlay and plug which is relatively inexpensive to manufacture, but which would protect the mesh and plug assembly during sterilization, shipping and handling, and which would further maintain the mesh in a substantially flat position and the plug in a substantially perpendicular position with respect to the mesh. The package should also be easily sterilizable and readily opened by operating room personnel in a sterile field in the operating room.

SUMMARY OF THE INVENTION

It is an objection of the present invention to provide a package for a mesh onlay and mesh plug assembly which will protect the assembly during sterilization, shipping, handling and storage and which will secure the mesh onlay in a substantially flat position while securing the mesh plug in a position substantially perpendicular to the mesh.

It is another object of the present invention to provide a package for a mesh onlay and plug assembly which is relatively inexpensive to manufacture.

It is another object of the present invention to provide a package for mesh onlay and plug assembly which is easily opened at the point of use in an operating room.

Accordingly, a package for holding a medical device, wherein the medical device comprises a flat mesh onlay having a mesh plug attached perpendicularly thereto, is disclosed. The package comprises a folder which comprises a central floor panel for receiving the mesh plug and mesh onlay. A first end panel is foldably connected to one end of the central floor panel for retaining the mesh onlay on the central floor panel in a substantially flat position when the first end panel is folded inward on top of the central floor panel. The first end panel is foldably connected to at least one reinforcing panel which when folded and locked into the first end panel with locking means provides structural integrity. A connecting panel foldably connected to the other end of the central panel floor is, in turn, foldably connected to an optional plug retaining panel. The optional plug retaining panel is in turn foldably connected to a second end panel. The plug is retained in a substantially perpendicular position with respect to the mesh onlay and the central floor panel when the connecting panel is folded inwardly, and the plug retaining panel is folded down and the second end panel is also folded down toward the first end panel. The first end panel is locked to the central floor panel with locking means. The second end panel is also locked to the central floor panel with locking means. The reinforcing panel when folded and locked has a structurally reinforcing configuration such as an A-frame.

Yet another aspect of the present invention is a method of packaging a mesh onlay and mesh plug assembly by inserting the assembly into the above-described package.

Other features and advantages of the invention will be more apparent from the following description and accompanying drawings.

BRIEF DESCRIPTION OF THE DRAWINGS

FIG. 3 is a perspective view of the reinforcing panels of the package of the present invention folded outwardly and locked into the first end panel.

FIG. 4 is a perspective view of the first end panel folded on top of the central panel and mesh onlay and mesh plug with the reinforcing panels folded and locked into the outer side of the first end panel.

FIG. 5 is a perspective view of an assembled package of the present invention containing a mesh onlay and mesh plug assembly.

BEST MODE FOR CARRYING OUT THE INVENTION

Figure 2:
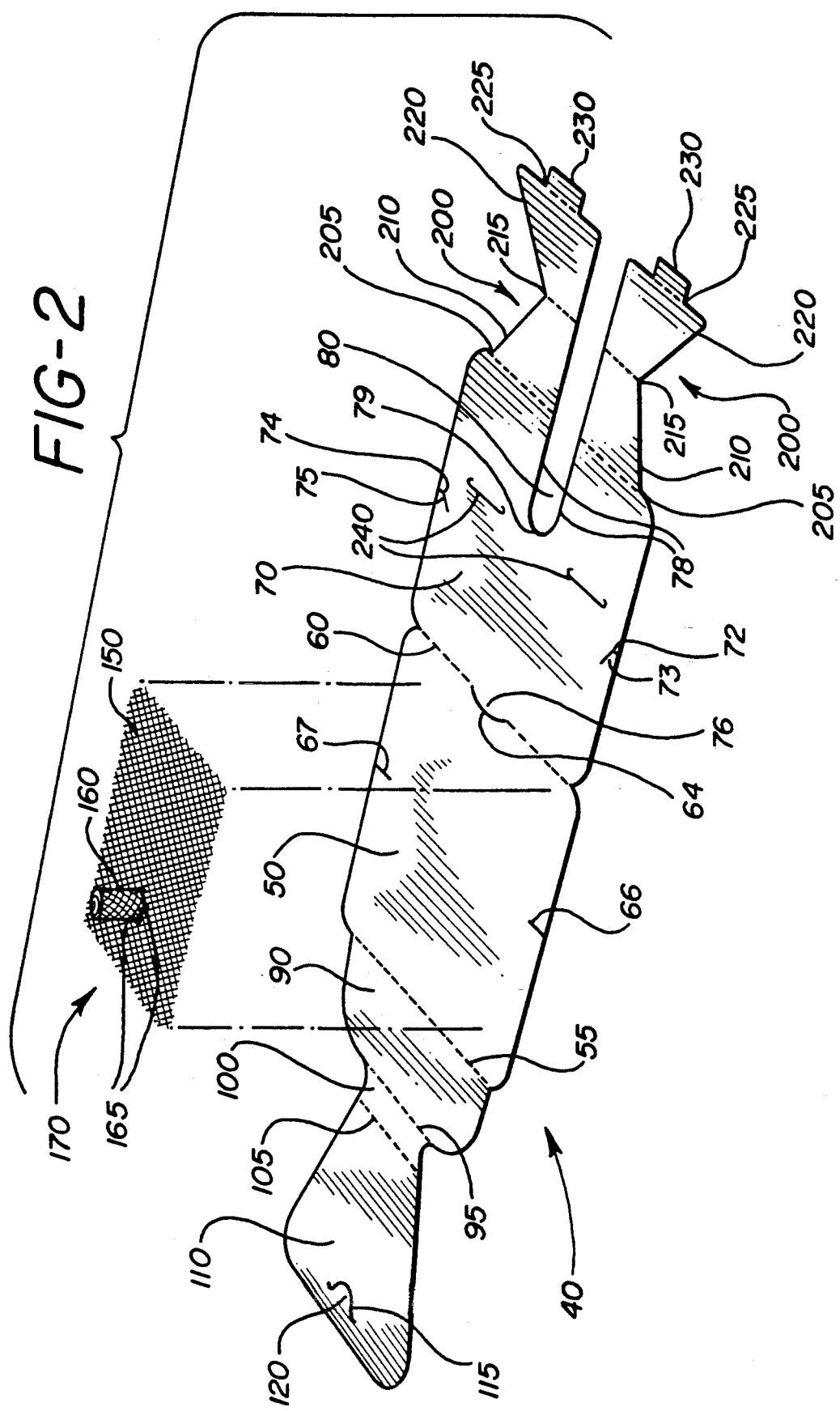
FIG. 2 is a perspective view of a mesh onlay and mesh plug assembly and the package of the present invention prior to assembly of the package.

A mesh plug and mesh onlay assembly 170 is shown in FIG. 2. The assembly 170 consists of substantially flat patch of mesh onlay 150 and rolled mesh plug 160. The plug 160 is affixed to mesh onlay 150 by suture material 165. Mesh onlay 150 is typically rectangular in shape, although it may have any shape including circular, square, elliptical and the like and combinations thereof, for example, one half of the onlay square and the other half having a circular shape. The dimensions of the onlay 150 and the plug 160 will be sufficient to effectively function as a supporting and plugging mechanism for hernia repair. Typically, the width of the onlay patch 150 is about 50 mm. The length of the onlay patch 150 is typically about 80 mm. The plug 160 will typically have a length of about 20 millimeters. The plug 160 will typically have a diameter of about 6 millimeters to about 8 millimeters. The onlay patch 150 will typically have a thickness in the range of about 0.027 inches.

The mesh used to construct the mesh onlay 150 and the mesh plug 160 may be any material which has the requisite biocompatibility requirements. It is particularly preferred to use a polypropylene mesh constructed of knitted filaments of extruded polypropylene. In order to attach the plug 160 to the onlay patch 150, it is preferred to sew the plug 160 to the onlay 150 using an appropriate conventional biocompatible suture material such as a non-absorbable, braided polyester fiber suture coated with a conventional suture coating. However, any conventional suture material or conventional attachment technique may be used. Examples of suitable attachment techniques include, but are not limited to, stapling, gluing, welding and the like.

Figure 1:
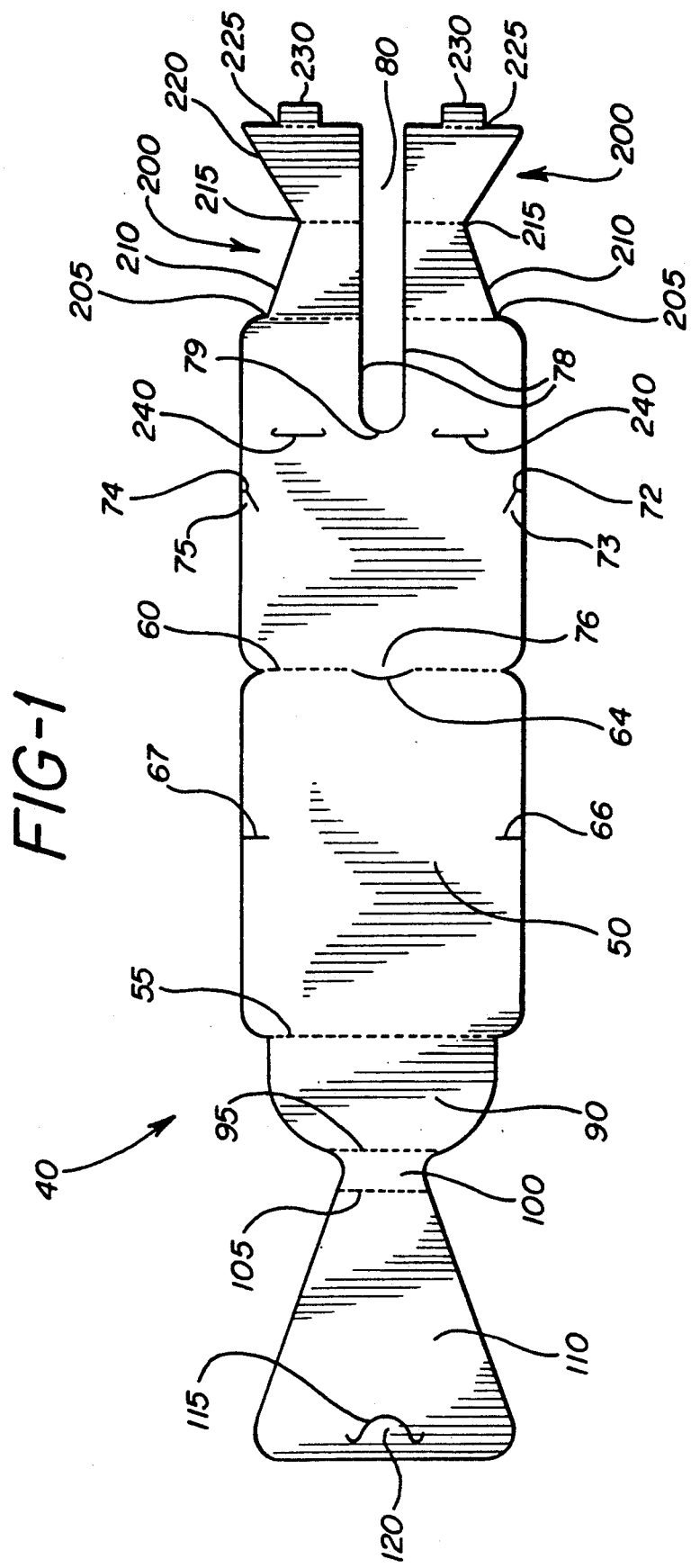
FIG. 1 is a plan view of the package of the present invention prior to folding.

Referring to FIG. 1 and FIG. 2, the package 40, prior to folding, is seen to have an inner, top surface and an outer, bottom surface. The package 40 has central floor panel 50 for receiving and holding mesh onlay and plug assembly 170. Central floor panel 50 is generally substantially rectangular in shape having two substantially parallel major sides and two substantially parallel minor sides. Central floor panel 50 has tab slots 66 and 67 centrally located opposite to each other and adjacent to the opposing major sides of panel 50. Central floor panel 50 is foldably connected to first end panel 70 along fold line 60 running along the first minor side of central panel 50. Central floor panel 50 also has slit 64 cut into said panel adjacent to fold line 60 to form tab pocket 76.

As can be seen in FIG. 1 and FIG. 2, first end panel 70 has a pair of opposed, substantially parallel, major sides and a pair of opposed, substantially parallel minor sides. The first end panel 70 is foldably connected to central floor panel 50 along its first minor side along fold line 60. The first end panel 70 has centrally opposed slits 72 and 74 centrally located along its major sides forming tabs 73 and 75 which, when first end panel 70 is folded on top of central floor panel 50, are aligned with and engaged by slots 66 and 67 to lock the panels together. Located at the second minor side of first end panel 70 is U-shaped slot 80 having straight sides 78 and curved end section 79. Slot 80 is sized to receive the mesh plug 160. Foldably connected to the second minor side of first end panel 70 about either side of slot 80 along fold lines 205 are a pair of reinforcing panels 200. Each reinforcing panel 200 has a first member panel 210 and a second member panel 220 and a tab 230. First member panel 210 is an irregularly shaped panel foldably connected on one end to first end panel 70 along fold line 205 and foldably connected at the opposite end to one end of second member panel 220 along fold line 215. Second member panel 220 is an irregularly shaped panel foldably connected on one end to first member panel 210 along fold line 215 and foldably connected along the other end to tab 230 along fold line 225. Tab 230 is preferably a rectangularly shaped panel foldably connected along fold line 225 to the other end of second member panel 220. First end panel 70 is also seen to have opposed slots 240 located at either side of curved end 79 of slot 80 for receiving mating tabs 230. It will be appreciated by those skilled in the art that, if one were willing to accept whatever disadvantages may be present, if any, the package 40 may have a single reinforcing panel 200. It will also be appreciated that the reinforcing panels 200 may comprise a plurality of member panels. For example, a reinforcing panel 200 having three foldably connected reinforcing panels would have a rectangular or channel configuration when folded.

Foldably connected to the other minor end of central floor panel 50 along fold line 55 is connecting panel 90, which in turn is foldably connected along fold line 95 to plug retaining panel 100, which is, in turn, foldably connected along fold line 105 to second end panel 110. Connecting panel 90 has curved top and bottom sides which meet at fold line 95. Optional plug retaining panel 100 is irregularly shaped and may if desired engage, when folded, the top of the outer side of the folded reinforcing panels 200.

Second end panel 110 is generally triangular in shape and has slit 115 centrally disposed toward its free end, which forms tab 120. If optional plug retaining panel 100 is not desired, then the second end panel 110 is foldably connected directly to connecting panel 90.

The package 40, as seen in FIG. 5, is assembled by initially centering the mesh onlay and plug assembly 170 on top of the inner surface of central floor panel 50 in a manner such that the major and minor axes of the mesh onlay patch 150 are substantially parallel to the major and minor sides of central floor panel 50. Then, as can be seen in FIG. 3, first member panel 210 and second member panel 220 of each reinforcing panel 200 are folded outwardly about fold lines 205 and 215. Then, tabs 230 are inserted into slots 240. Next, as can be seen in FIG. 4, first end panel 70 is folded inwardly along fold line 60 over the mesh onlay patch and plug assembly 170 so that plug 160 is received by slot 80, and male tabs 73 and 75 are locked into slots 67 and 66. First end panel 70 is retained in a position substantially parallel to the central floor panel 50 by the tabs 73 and 75. Next, connecting panel 90 is folded inwardly toward central floor panel 50 along fold line 55, and optional plug retaining panel 100 is folded down along fold line 95 so that, if desired, the inner surface of plug retaining panel 100 engages the top sections of reinforcing panels 200. Then, second end panel 110 is folded down toward first end panel 70 and male tab 120 is inserted into, and engaged by, tab pocket 76. The package 40 may then be placed into a conventional plastic envelope or foil pouch (not shown), which is then sealed. The sealed package is then typically processed in a conventional sterilization process and further packaged for shipping and storage. Although tabs and slots are used to lock the panels of package 40, other conventional locking means such as adhesives, mechanical fasteners, etc., could be used if one were willing to accept any disadvantages attendant therewith.

The package 40 of the present invention may be made from any material which can be readily die cut and scored and which can be folded and sterilized. These materials include paper, plastic, foils, and laminates of one or more thereof. However, it is particularly preferred in the practice of the present invention to utilize a heavy weight, relatively stiff, medical grade paper or paper board such as 9 pt. medical grade sulfate. The packages are preferably stamped from sheets of material using a conventional die press apparatus, such as a platen press.

It will be appreciated by those skilled in the art that the sizes of panels of the package 40 of the present invention will vary in accordance with the size and shape of the mesh onlay and plug assembly 170. Preferably, the panels will be sufficiently large to effectively contain the assembly 170 within the folded package 40, as seen in FIG. 5.

Referring to FIG. 5, it can be seen that the package 40 of the present invention, when assembled and locked, has a triangular-like elevation. The assembled package 40 also has a pyramidal-like shape when viewed in perspective. The reinforcing panels 200 are seen to have a triangular truss-like profile or an A-frame type configuration. The reinforcing panels 200 contribute structural strength to the package 40 by making it more crush resistant. In addition, the assembly 170 is seen to be partially visible, e.g., the plug 160 and a portion of the mesh onlay 150. It is surprising that the unfolded, two-dimensional, flat package 40 as seen in FIG. 1 can be processed into the assembled package 40 of FIG. 5 having a pyramidal-like, three-dimensional shape.

It will be appreciated by those skilled in the art that it particularly difficult to retain the flexible mesh onlay 150 in a substantially flat position and the flexible mesh plug 160 in a substantially perpendicular position, with respect thereto, in a one-piece package which is easy and economical to manufacture. Conventional packages for medical devices may retain a device in a given spatial configuration but are frequently difficult to open and may require a time consuming delicate procedure to effectively remove the medical device from the package without damaging the medical device. Such packages are typically complex, costly, and have multiple pieces.

The one-piece package 40 of the present invention is easy and economical to manufacture using conventional fabrication materials and techniques. The package protects the mesh onlay and mesh plug assembly 170 during sterilization, shipping and handling. The package 40 maintains the mesh onlay 150 in a substantially flat position and the mesh plug 160 in a substantially perpendicular position with respect to the mesh onlay 150 so that the assembly 170 is useable for its intended purposes in a hernia repair operation. In addition, when viewing the assembled package 40, the assembly 170 can be seen, in part, from an exterior perspective. Also, the assembled, pyramidal-like configured package 40, having reinforcing panels 200 forming a structural configuration, is easily inserted into a pouch or envelope for sterilization. This is typically a tedious procedure since the envelope or pouch has, basically, a two-dimensional configuration.

The package 40 is extremely easy to open and the mesh onlay and mesh plug assembly is easily removed in a hospital in the sterile area of an operating room.

Although this invention has been shown and described with respect to the detailed embodiments thereof, it will be understood by those skilled in the art that various changes in form and detail thereof may be made without departing from the spirit and scope of the claimed invention.

What is claimed is:

1. A folder package for holding a mesh onlay and mesh plug assembly, comprising:
   a central floor panel for receiving the mesh onlay and mesh plug assembly, said panel having a pair of opposed major sides and a pair of opposed minor sides;
   a first end panel having a pair of opposed minor sides and a pair of opposed major sides foldably connected along a first minor side to one minor side of the central panel for retaining the mesh onlay in a substantially flat position on the central panel;
   at least one reinforcing panel foldably connected to the other minor side of the first end panel for providing structural strength to the package, wherein the reinforcing panel comprises a first member panel foldably connected to the first end panel and a second member panel foldably connected to the first member panel;
   a second end panel foldably attached to the other minor side of the central panel;
   a connecting panel foldably connected to the central floor panel along the opposite minor side of the floor panel and also foldably connected to the second end panel wherein the second end panel is foldably attached to the connecting panel;
   locking means for locking the first end panel to the central floor panel wherein the locking means for locking the first end panel to the central floor panel comprises a pair of opposed slits located along the major sides of the central floor panel and, a mating pair of tabs located in the first end panel;
   locking means for locking the second end panel to the central floor panel; and
   locking means for locking each reinforcing panel to the first end panel.

2. The folder package of claim 1 wherein the locking means for each reinforcing panel comprises at least one slit in the first end panel and a mating tab connected to each reinforcing panel.

3. The folder package of claim 1 wherein the locking means for the second end panel comprises:
   a slit in the central floor panel adjacent to the first end panel, said slit forming a pocket slot; and,
   a second slit in the second end panel, said second slit forming a tab which is engaged by said pocket slot.

4. The folder package of claim 1, further comprising a slot in the first end panel for spatially retaining the mesh plug with respect to the central panel.

5. A folder package for holding a mesh onlay and mesh plug assembly, comprising:

a central floor panel for receiving the mesh onlay and mesh plug having a pair of opposed major sides and a pair of opposed minor sides;

a first end panel having a pair of opposed major sides and a pair of opposed minor sides foldably connected along a first minor side to one minor side of the central panel for retaining the mesh onlay in a substantially flat position;

at least one reinforcing panel foldably connected to the other minor side of the first end panel for providing structural strength to the package;

a connecting panel foldably connected to the opposite minor sides of the central panel;

a second end panel;

locking means for locking the first end panel to the central floor panel;

locking means for locking the second end panel to the central floor panel wherein the locking means for locking the first end panel to the central floor panel comprises a pair of opposed slits, located along the major sides of the central floor panel and, a mating pair of opposed tabs located in the first end panel;

locking means for locking each reinforcing panel to the first end panel; and a plug retaining panel foldably connected between the connecting panel and the second end panel.

6. The package of claim 5 wherein the locking means for the second end panel comprises:

a slit in the central floor adjacent to the first end panel, said slit forming a pocket slot; and a second slit in the second end panel, said second slit forming a tab which is engaged by said pocket slot.

7. The package of claim 5, further comprising a slot in the first end panel for spatially retaining the mesh plug with respect to the central floor panel.

8. The package of claim 5 wherein the reinforcing panel comprises at least two foldably connected member panels.

9. The package of claim 8 wherein the reinforcing panels when folded and locked have an A-frame configuration.

10. The package of claim 5 wherein the locking means for locking the at least one reinforcing panel comprises a tab connected to each reinforcing panel and a mating slot in the first end panel for each such tab.

11. The package of claim 5 additionally comprising a plug retaining panel foldably connected between the connecting panel and the second end panel.

* * * * *